United States Patent [19]
Clark et al.

[11] Patent Number: 5,900,371
[45] Date of Patent: * May 4, 1999

[54] METAL COMPLEXED SERINE PROTEASE INHIBITORS

[75] Inventors: James M. Clark, San Mateo; Thomas E. Jenkins, LaHonda; Bradley A. Katz; Robert M. Stroud, both of San Francisco, all of Calif.

[73] Assignees: Axys Pharmaceuticals Inc., San Francisco; The Regents of the University of California, Oakland, both of Calif.

[ * ] Notice: This patent is subject to a terminal disclaimer.

[21] Appl. No.: 08/925,844

[22] Filed: Sep. 8, 1997

Related U.S. Application Data

[63] Continuation of application No. 08/430,742, Apr. 28, 1995, Pat. No. 5,693,515.

[51] Int. Cl.$^6$ .............................. C12N 9/76; C12N 11/08; C12N 9/99
[52] U.S. Cl. ......................... 435/184; 435/180; 435/183; 435/213; 514/184
[58] Field of Search ................................... 435/180, 183, 435/184, 213; 213/184

[56] References Cited

U.S. PATENT DOCUMENTS

| | | |
|---|---|---|
| 3,646,049 | 2/1972 | Hoff et al. . |
| 4,621,080 | 11/1986 | Dombay et al. . |
| 4,935,493 | 6/1990 | Bachovchin et al. . |
| 4,940,723 | 7/1990 | Tidwell et al. . |

FOREIGN PATENT DOCUMENTS

| | | |
|---|---|---|
| 0 291 304 | 11/1988 | European Pat. Off. . |
| WO 95/08540 | 3/1995 | WIPO . |
| WO 95/14788 | 6/1995 | WIPO . |
| WO 95/19772 | 7/1995 | WIPO . |
| WO 96/06831 | 3/1996 | WIPO . |
| WO 96/18402 | 6/1996 | WIPO . |

OTHER PUBLICATIONS

Tidwell et al., "Diarylamidine Derivatives With One or Both of The Aryl Moieties Consisting of an indole or indole–like Ring, Inhibitors of Arginine–specific Esteroproteases" (1978) *Journal of Medicinal Chemistry*, vol. 21, No. 7:612–623.

Brothers II et al., "Catalytic Activity of The Serine Proteases A–Lytic Protease Tagged at The Active Site With a (Terpyridine)platinum(II) Chromophore" (1990) *Biochemistry*, 29:7468–7474.

Kang, "Human Neutrophil Elastase: Rapid Purification, Metal Binding Stoichiometry And Modulation of The Activity by Chelating Agents" (1988). *Korean J. of Pharmacology*, vol. 24, No. 1:111–123.

Kelly et al., "Interaction Between Non–Classical B–lactam Compounds And The $Zn^{2+}$–containing G And Serine R61 And R39 D–alanyl–d–alanine Peptidases" (1981) *Biochem., J.*, 199:129–136.

Almenoff et al., "Identification of a Thermolysin–like Metalloendopeptidase in Serum: Activity in Normal Subjects And in Patients With Sarcoidosis" (1994) *J. Lab and Clinical Medicine*, Vol. 103, No. 3:420–431.

Lombardy et al., "Synthesis and DNA Interactions of Benzimidazole Dications Which Have Activity Against Opportunistic Infections," *J. Med. Chem* (1996), 39:1452–1462.

Fairley et al., "Structure, DNA Minor Groove Binding, and Base Pair Specificity of Alkyl–and Aryl–Linked Bis(amidinobenzimidazoles) and Bis(amidinoindoles)," *J. Med. Chem.* (1993), 36: 1746–1753.

Higaki, et al., "Regulation of Serine Protease Activity by an Engineered Metal Switch", *Biochemistry* 1990, vol. 29, pp. 8582–8586.

Gafarova, et al., "Cobalt Complex of di:benzimidazole di:benzoyl methane used as an active catalyst in oxidation hexadecane hydroxy carboxylic acid", Derwent AN82–21597E Abstract; May 1981; 1 page.

*Primary Examiner*—Herbert J. Lilling
*Attorney, Agent, or Firm*—Townsend & Townsend & Crew, LLP; Karen B. Dow

[57] ABSTRACT

Serine protease inhibitors are provided comprising compounds having a P site binding moiety and a divalent cation(s) chelating moiety which are pre-prepared as divalent cation(s) complexes or combined with the serine protease in the presence of divalent cation(s). The compounds are shown to have high inhibitory activity when complexed to divalent cation(s) and find use in various processes associated with serine protease isolation and inhibition.

2 Claims, No Drawings

METAL COMPLEXED SERINE PROTEASE INHIBITORS

This is a continuation of application Ser. No. 08/430,742, filed Apr. 28, 1995 now U.S. Pat. No. 5,693,515.

TECHNICAL FIELD

The field of this invention is serine protease inhibitors.

BACKGROUND

Serine proteases are universally found in living organisms, fulfilling a wide variety of functions. In many cases, the serine proteases have specific targets, where precursors are activated to biologically competent products to discharge their particular function. In other cases, there is a more generalized activity, where particular dipeptide sequences within larger proteins are subject to scission in the process of degradation.

Among important serine proteases are trypsin-like enzymes, such as trypsin, tryptase, thrombin, kallikrein, and factor Xa. The serine protease targets are associated with processes such as blood clotting, complement mediated lysis, the immune response, glomerulonephritis, pain sensing, inflammation, pancreatitis, cancer, regulating fertilization, bacterial infection and viral maturation. By inhibiting serine proteases which have high specificity for a particular target, one can inhibit in vivo numerous biological processes, which may have adverse effects on a host.

The serine proteases have a highly conserved active site, where specific amino acids which catalyze the bond scission have a nearly identical spatial arrangement. A complementary binding site adjacent to the active site provides for the primary specificity of the individual serine protease. A succession of indentations or "pockets" along the surface of the protease serve to bind successive side chains along the substrate polypeptide chain on either side of the peptide bond to be cleaved. These are described as P3, P2, P1 prior to the susceptible peptide bond, and P1', P2', P3' after the scissile bond in the substrate, when the peptide sequence is represented in the customary N-to-C terminal manner. Therefore, by providing recognition elements similar to specific amino acid side chains found in the substrate peptide sequences having high affinity to the pockets, one can direct moieties capable of occupying the pocket of the active site to specific serine proteases, so as to restrict the pathways which are inhibited. There is, therefore, substantial interest in identifying inhibitors for the catalytic active site of serine proteases which may be joined to moieties providing specificity for a particular protease.

Relevant Literature

Tidwell et al., J. Med. Chem. (1978) 21:613–623; Geratz et al., Arch. Biochem. Biophys. (1979) 197:551–559; and U.S. Pat. No. 4,940,723 describe bis-(5-amidino-2-benzimidazoylyl)methane and analogs thereof as serine protease inhibitors. Higaki et al., Biochemistry (1990) 29:8582–8586; Kang, Korean J. of Pharmacology (1988) 24:111–123; and Kelly et al., Biochem. J. (1981) 199:129–136 report instances of serine proteases involving the use of zinc.

SUMMARY OF THE INVENTION

Methods and compositions are provided for the modulation of serine protease activity. Compounds are provided, which in combination with divalent metal cations, most preferably zinc or cobalt, or as the metal cation complexes are used to inhibit one or more serine proteases. The compounds comprise a P1 binding moiety and a metal chelating moiety joined by a linking group and spaced apart to fit in the active site of the target serine protease. The compounds find use in the inhibition of serine proteases in vitro and in vivo, in assays and in the protection of peptides and proteins from proteolytic degradation. Moreover, since zinc is one of the more common divalent metal ions present in physiological tissues and fluids, usually at 10–100 $\mu$M concentration, the most preferred embodiment of this invention includes zinc as the divalent metal cation.

DESCRIPTION OF THE SPECIFIC EMBODIMENTS

Methods and compounds used therein are provided for inhibition of serine proteases, particularly trypsin-like serine proteases. These enzymes may differ as to sequence depending upon the particular source, whether prokaryotic or eukaryotic, the tissue from an animal source, mutants, and the like. Inhibition is achieved by contacting the target serine protease with the inhibiting compound in the presence of a physiologically acceptable metal ion mediator, particularly divalent metal ion, more particularly zinc or cobalt, particularly added metal ion for known inhibitors, or as a preformed complex. The inhibitor is characterized by having two heteroatoms which are able to complex the metal ion by having unshared pairs of electrons. Inhibition employing known inhibitors of this structural class can be substantially enhanced by providing pre-formed complexes with the metal ion or adding the metal ion to the medium in sufficient amount to provide the enhanced inhibition. Alternatively, in vitro or in vivo, where the minimum amount of zinc is present, the inhibitor need only be added to the target serine protease to provide for the enhanced inhibitory activity resulting from the zinc complex.

Since zinc is the preferred metal ion and is present in physiological samples, hereafter zinc will be used as exemplary of metal ions generally, particularly exemplary of cobalt.

The zinc complexes of this invention may be characterized by the following formula:

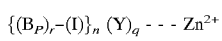

wherein:

B$_P$ intends the binding moiety for binding to one or more of the P sites, particularly at least P1;

I is a moiety that comprises at least one heteroatom, which is oxygen, sulfur or nitrogen and when n is 1, comprises at least two heteroatoms, spaced apart so as to be able to chelate zinc, or when n=2, has at least one heteroatom, so that the two groups joined by Y are capable of chelating zinc in a bidentate manner, thus providing two of the four coordinating ligands around zinc;

Y is a bond or linking group of not more than six, usually not more than three atoms in the chain, particularly carbon, which provides that the spacing when the two Is are bound to Y provides chelation of zinc; r is 0 to 1, wherein the sum total of r's is at least 1;

n is one to two, and q is zero when n is one and one when n is two.

When n is 2, illustrative compounds will preferably come within the following formula:

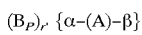

wherein:

α is a heterocycle having at least one heteroatom, which is N, O or S, or is a cyclic aromatic ring with one of these heteroatoms directly attached, is of at least 2 carbon atoms and not more than 36 carbon atoms, usually not more than 18 carbon atoms, preferably not more than 12 carbon atoms, may be mono- or polycyclic, fused or non-fused, where the individual rings will usually be of from 4 to 7, more usually 5 to 6 annular members, may include aliphatic unsaturation, wherein a heteroatom is within 3 atoms, usually within 2 atoms, and preferably within 1 atom of A; there being from about 1 to 4, usually 1 to 3 and preferably 1 to 2 annular heteroatoms, generally not more than 8 heteroatoms, more usually not more than 6 heteroatoms total;

A is a bond or a linking group of from 1 to 2 atoms, usually 1 atom, which are C, N, O or S, where any remaining valences are satisfied by H, alkyl of from 1 to 2 carbon atoms, oxo, oxy of from 0 to 2 carbon atoms, halo, amino of from 0 to 2 carbon atoms, and thiol, wherein heteroatoms are bonded only to carbon, hydrogen and oxygen, particularly carbon and hydrogen;

β comprises a heterosubstituted carbon ring bonded directly or indirectly to A, where the heteroatom is N, O or S; β may be the same or different from a, is of from about 1 to 36, usually 2 to 30, more usually 3 to 18 carbon atoms, may be aliphatic, alicyclic, aromatic, heterocyclic, or combinations thereof, the number of heteroatoms coming within the definition for a when a heterocycle, otherwise having from about 1 to 6, usually 1 to 4 heteroatoms as defined above, and wherein the heteroatom bonded to the carbon is not more than 6 atoms, usually not more than 4 atoms from the heteroatom of a within 3 atoms of A; β may include aliphatic unsaturation, ethylenic or acetylenic, aromatic unsaturation, or be saturated; and wherein the two related heteroatoms are positioned to be able to occupy the coordinate complex (dsp²) chelating sites of zinc;

r' is 1 or 2;

$B_P$ is the moiety binding to the P site of the serine protease and is bound to α and/or β in appropriate spatial relationship for binding to the serine protease, usually from about 1 to 6, more usually from about 2 to 4 atoms away from the heteroatoms of α and/or β in positional relationship to A.

α and/or β heterocycles of interest preferably have at least one sp² nitrogen atom, include 5 membered rings, such as pyrazole, imidazole, triazole, oxazole, thiazole, isoxazole, etc.; benzo-fused derivatives thereof, such as benzimidazole, etc.; six membered rings, such as pyran, pyridine, pyridazine, pyrimidine, pyrazine, dioxane, etc.; benz derivatives thereof, such as quinoline, isoquinoline, cinnoline, etc.; non-fused rings, such as 2,2'-bis-imidazole, 2,2'-bis-pyridine, etc. Substituents may include halogen, oxy, amino, cyano, non-oxocarbonyl, alkyl, or any other common substituent, preferably electron-donating, which does not sterically preclude binding or complexation steps necessary for the inhibitor to function.

When other than a heterocycle, β can be methoxymethyl, aminomethyl, methylaminomethyl, guanidinyl, anilinomethyl, 2,3-diaminopropyl, 2-amino-3-hydroxypropyl, 2-amino-2-trifluoromethylethyl, 2-hydroxyethyl, substituted aromatics like 2-mercaptophenyl, 2-hydroxyphenyl, 2-aminophenyl, 2-carboxyphenyl and substituted analogs thereof, methylacetoxy, glycinamidomethyl, cyclohexylaminomethyl, and the like.

The subject compounds may have one or more heteroatom containing substituents other than the heteroatoms involved in chelating. The substituents will usually be not more than 6 carbon atoms, more usually not more than 3 carbon atoms and may include amino of from 0 to 6 carbon atoms, non-oxo-carbonyl of from 1 to 6 carbon atoms, particularly salts, esters and amides, and the sulfur and nitrogen analogs thereof, oxy or alkyloxy of from 0 to 6 carbon atoms, or aryloxy, halo, cyano, nitro, oxo, etc.

$B_P$ can be guanidine, amidine, aminomethyl, amino higher alkyl, α-aminocarboxymethyl, α-aminocarboxamidemethyl, etc.

Compounds of particular interest include 5-substituted 2,2'-bis-benzimidazoles, where the 5-substituent is any basic group bonded to the basic heteroatom or group through a carbon, where the substituent will usually be not more than 10 atoms other than hydrogen, more usually not more than 6 atoms other than hydrogen, generally composed of carbon, hydrogen, nitrogen and oxygen. The other imidazole ring may also be substituted with alkyl, non-oxo carbonyl, amino, aminoalkyl, amidinyl, or the like, generally of not more than 12 atoms other than hydrogen, more usually not more than 6 atoms other than hydrogen.

When n is one, compounds of particular interest will have the following formula:

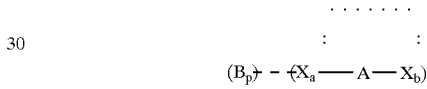

wherein:

$B_P$ has been defined previously;

A is a bond or linking group having one to four atoms in the chain, normally carbon or heteroatom, more usually one to two atoms, where the heteroatoms are particularly oxygen, sulfur or nitrogen; the linking group may be substituted by other atoms, particularly to maintain the chelating heteroatoms in position to chelate with zinc; A may be aliphatic, aromatic, alicyclic, heterocyclic or combinations thereof, and may be taken together with the heteroatoms to which it is attached to form a ring, wherein the broken line indicates that the heteroatoms may be part of a heterocyclic ring; and $X_a$ and $X_b$ are oxygen, sulfur and nitrogen, particularly sp²-hybridized nitrogen, spaced apart so as to be capable of chelating zinc, bonded to carbon, hydrogen and oxygen, particularly carbon and hydrogen; and may be annular heteroatoms or substituted directly or indirectly to an annular atom. Of particular interest are compounds where the heteroatom is a heteroannular atom of a ring of from 4 to 7, preferably from 5 to 6 heteroannular members, there usually being at least 2, more usually at least 3 carbon atoms in the ring, the remaining atoms being the heteroatoms mentioned heretofore.

The compounds may be aliphatic compounds, where the heteroatoms are flexible or held in spatial relationship by the presence of unsaturation in the linking group, e.g. ethylenic unsaturation, or being held in position by being bonded, either directly or through a carbon atom to a ring of from 3 to 7 members; the heteroatoms and linking group may be part of a heterocyclic ring, such as in benzimidazole or pyrimidine. The significant factor is that the required chelating atoms may be members of different non-fused rings.

The heteroatoms for chelating will generally be separated by at least 2 other atoms and not more than 4 other atoms, usually not more than 3 other atoms, the other atoms usually being carbon. The atoms may be non-annular, annular, or combinations thereof. Of particular interest is where nitrogen is a heteroannular member of a 5 to 6 membered ring, where the ring has 2 nitrogen atoms separated by a carbon atom, particularly where there is a double bond between the intervening carbon atom and a nitrogen atom. Also of particular interest, are rings, as described above, joined together by a bond of from 1 to 2 atoms, particularly 1 atom, where such linking group may be a carbon atom, substituted carbon atom, or heteroatom, particularly nitrogen, oxygen and sulfur. Desirably, the linking group is alpha to a nitrogen atom, more particularly where there are 2 nitrogen atoms separated by an intervening carbon atom, and bonded to the intervening carbon atom.

The binding portion of the molecule which fits into the P site, particularly the P1 site, may be an amino acid, particularly arginine or lysine, may be an oligopeptide which is the specific target site for this target serine protease, may be preferably amidine, amino, guanidino, or other basic moiety for trypsin-like serine protease, carboxylates or lipophilic groups for chymotrypsin-like proteases.

For the most part, the compounds of this invention will be fewer than 60 carbon atoms, more usually fewer than 36 carbon atoms, particularly fewer than 18 carbon atoms, more particularly fewer than 12 carbon atoms, having fewer than 20 heteroatoms, frequently fewer than 16 heteroatoms, generally fewer than about 12 heteroatoms, particularly not more than about 8 heteroatoms, frequently not more than about 7 heteroatoms. Particularly, where the binding moiety is other than oligopeptide, the number of heteroatoms in the molecule will be not more than 12, more usually not more than 8, generally there being at least 2 heteroatoms, more usually at least 4 heteroatoms.

Where 2 rings are joined by a linking group to form the chelating moiety, the linking group may be methylene, methene, carbonyl, amino, oxy, thio, isopropylidene, etc.

Instead of having 2 entities joined together by a linking group, one may provide for a single entity particularly fused polycyclics, having heteroatoms at appropriate positions. Compounds of interest include 1,8-diaminonaphthalene, 8-cinnoline, 5,6-diaminophenanthrene, 1,8-dihydroxynaphthalene, and the like, where the positioning of the heteroatoms for chelation corresponds to the definitions described above for the heterocycle.

Compounds of interest include, but are not limited to:
5,5'-bis (amidinobenzimidazole) methane (BABIM);
5,5'-bis (amidinobenzimidazole) carbonyl;
2-(2'-(5'-aminomethyl)benzimidazolyl)methylbenzimidazole;
2-(2'-(5'-aminomethyl)benzimidazolyl)methyl-5-methylbenzimidazole;
2-(2'-(5'-amidino)benzimidazolyl)methylbenzimidazole;
2-(2'-benzimidazolyl)methylbenzimidazole;
2-(2'-(5'-guanidino)benzimidazolyl)methylbenzimidazole;
2-(2'-(5'-carboxy)benzimidazolyl)methylbenzimidazole;
2-(2'-(5'-amidino)benzimidazolyl)methylimidazole;
4-(2'-(5'-amidino)benzimidazolyl)methylimidazole;
2-(2'-(5'-amidino)benzimidazolyl)pyridine;
2-(2'-(5'-amidino)benzimidazolyl)methylpyridine;
1-(2'-(5'-amidino)benzimidazolyl)isoquinoline;
2-(2'-(5'-amidino)benzimidazolyl)quinoline;
3-(2'-(5'-amidino)benzimidazolyl)isoquinoline;
8-(2'-(5'-amidino)benzimidazolyl)quinoline;
5-amidino-(2'-hydroxyphenyl)benzimidazole;
5-amidino-(2'-mercaptophenyl)benzimidzole; and
5-amidino-(2'-aminophenyl)benzimidazole.

The subject compounds can be used in conjunction with zinc to inhibit serine protease enzymes, where one compound may be preferred in conjunction with a particular serine protease.

The subject compounds can be prepared in accordance with known synthetic procedures. See, for example, Tidwell, et al., J. Med. Chem. (1978) 21:613–623; and general methods for the synthesis of substituted and/or fused heterocyclic systems and their isomers, as described in "Comprehensive Heterocyclic Chemistry", Pergamon Press:Oxford, 1988.

The subject compounds may be prepared as crude mixtures comprising at least about 50 weight %, usually at least about 90 weight % of the composition. Preferably, the subject compounds will be at least about 99 weight % of the composition. Similarly, the zinc complexes may be prepared and have the same purity ranges. Also, when using the subject compositions, particularly as the zinc complex, the composition may be complexed with a target serine protease. This zinc complex may be formed in relation to inhibiting the serine protease, as an inhibited enzyme composition which may be activated upon removal of the zinc from the serine protease complex with a chelating agent, or the like. The serine protease-inhibitor composition may also come within the same purity ranges as indicated above for the inhibitor.

The zinc complex may be pre-prepared and isolated by combining the subject compound with zinc at a concentration of at least about 0.01 $\mu$M, usually at least about 0.1 $\mu$M, more usually 5 $\mu$M, preferably at least about 50 $\mu$M or higher, depending upon the particular compound and its $K_i$. Usually, the zinc concentration will be less than about 100 mM, more usually less than about 50 mM, and generally more than about 1 $\mu$M. Generally, the amount of zinc which is added to a preparation or medium containing the inhibitor will be sufficient to increase the zinc concentration by at least about 0.1 nM, more usually at least about 1 $\mu$M, generally at least about 50 $\mu$M, and usually not more than about 1 mM. Conveniently, the zinc concentration employed will provide that at least about 80%, preferably at least about 90%, and more preferably substantially all of the inhibitor will be chelated with zinc. In physiological systems, the amount of zinc present will normally be sufficient to provide the zinc complex, although pre-preparation of the zinc complex may enhance the inhibitory efficiency of the subject compounds.

Compounds sufficiently satisfying the structural criteria described above may be determined by use of an in vitro assay system which measures the potentiation of inhibition of any serine protease by a compound of the present invention in both the presence and absence of physiologically relevant concentrations of zinc. Standard assay formats for measurement of specific serine protease activity utilize the enzyme of choice and short peptide substrates whose cleavage can be quantitated, usually by simple calorimetric methods. This assay system can be configured in three formats to detect if a compound satisfies the structural requirements for inhibition potentiation in the presence of zinc. The assay formats are:

(a) determination of the inhibition level (indicated by Ki (Baseline)) without regard to adjustment of zinc levels (i.e., ambient levels present in reagents and distilled water);

(b) determination of the Ki (Zinc removed) in the enforced absence of the zinc by addition of an excess of EDTA, phenanthroline, or any other common cation sequestering agent which has no effect on the protease activity on its own;

(c) determination of the Ki (zinc added) in the presence of the added zinc to adjust the assay concentration into a physiologically relevant concentration range; animal plasma, including human plasma, can also be utilized in the assay medium to provide physiologically relevant levels of zinc.

A compound successfully fulfulls the structural requirements described above only if the value of the Ki (Zinc removed) >>Ki (Zinc added), indicating inhibition is potentiated (i.e., the compound is a more potent inhibitor) in the presence of zinc. The assay formats described above are given as Examples below.

The assay system developed to explain the enhanced activity of a compound of the current invention in the presence of added zinc can thus be used to discover new serine protease inhibitors of enhanced potency, in which a P1 serine protease recognition element (itself a potential weak inhibitor) and the bidentate chelator derived from electron-rich heteroaromatic functionalities have been correctly incorporated into a new composition. The compounds of the current invention are a new class of serine protease inhibitors which are composed of the following two elements:

(a) a chemical function group which occupies the P1 site on the target serine protease, which alone could be a serine protease inhibitor; and (b) a structurally adjacent bidentate chelator which captures a divalent cation, such as zinc, into a complex involving His57 and Ser195 of the catalytic site of the enzyme. Combination of these dual features into a single composition provides effective serine protease inhibition at physiological levels of divalent cations like zinc.

The component chemical functional moieties necessary for the zinc potentiation of inhibition can also be tested separately to show that efficient and potentiated inhibition of serine proteases is only observed when the proper combination of these moieties into one compound has been accomplished. For example, for the compound 2-(2'-(5'-amidino)benzimidazolyl) pyridine, the component functional moieties can be formulated as benzamidine as the P1 recognition element and 2-(2'-pyridyl)benzimidazole, a known, commercially available zinc sequestering agent, as the chelating moiety. In vitro assays using the three systems described above clearly show that benzamidine is a weak inhibitor of the serine protease trypsin, and that 2-(2'-pyridyl)benzimidazole shows no inhibition activity. However, the proper structural combination of these chemical functional groups into a single compound, 2-(2'-5-amidino)benzimidazolyl) pyridine, clearly shows that a significant potentiation of serine protease inhibition has been accomplished when the compound is evaluated in the presence of physiological levels of zinc. Other Examples of the application of the design requirements for compounds of the current invention are given below.

Finally, x-ray crystallography of the inhibitor-zinc-serine protease complexes can be obtained by one skilled in the art using contemporary biophysical methodologies and commercial instrumentation. Such crystallographic data can be used to conclusively determine if a composition of the current invention has embodied the structural requirements necessary for zinc potentiation of serine protease inhibition. An example of such an X-ray crystallographic determination is presented below.

Serine protease enzymes of interest include, but are not limited to, trypsin-like enzymes, such as trypsin, kallikrein, plasmin, thrombin, and tryptase; chymotrypsin-like enzymes, including chymotrypsin, cathepsin G, and chymase; elastase-like enzymes, including neutrophil elastase and elastase; and carboxypeptidase-like enzymes. These enzymes play a role in apoptosis, blood pressure regulation, cancer, cardiovascular function, blood clotting, lysis, chemotaxis, development, digestion, fertilization, hormone processing, immune response, complement, infection: bacterial, viral, and parasitic; inflammation, mast cells, and other cells, neurologic, pain and protein secretion. Serine protease targets in medicine include for cardiovascular treatments: thrombin, factor Xa, factor VIIa, and chymase; for infectious diseases involving parasites, viruses and bacteria, serine proteases specific for the pathogen; for bleeding, urokinase, and tPA; for inflammation, tryptase, chymase, neutrophil elastase, and kallikrein; and for neurobiology, serine proteases associated with Alzheimer's disease, to name only a few of the available targets.

The subject compositions may be used in a variety of ways, in vitro and in vivo. By linking the subject compositions at a site which does not interfere with their binding to serine proteases, the subject compositions may be used in affinity columns to isolate serine proteases. Particularly, since the subject compounds vary as to their affinity to specific proteases, the subject compositions can be selective in the isolation and purification of serine proteases.

Conventional techniques may be employed for linking the various compounds to supports, beads, macromolecules, and the like. Linking groups may include carboxyl groups, amino groups, thio groups, activated olefins, or the like. The linking group may be bonded to the inhibition moiety or the binding moiety. Surfaces of columns or capillaries may be employed as the affinity column or the column may be packed with a variety of beads, such as Sephadex, sepharose, latex beads, or the like. The particular manner in which the column is prepared is not critical to this invention. In addition, the columns may be used in assays for detecting the various serine proteases, by providing a binding profile which can be developed for the serine protease of interest.

The subject compositions may be also used in conjunction with substrates for a specific serine protease, where one wishes to maintain the integrity of the substrate in the presence of the serine protease. Thus, if one wishes to inhibit clotting as a result of thrombin activation of fibrinogen, one can employ one of the subject compounds in conjunction with zinc to prevent the activation of the clotting cascade, retaining the various members of the clotting cascade as precursors. In this manner, one can monitor the amount of fibrinogen in a blood sample and when one wishes to initiate the clotting cascade, add chelating agents to remove the zinc from involvement in the inhibitor complex with the serine proteases present in the sample.

One may also use physiologically acceptable serine protease inhibitors for the treatment of various indications. As described in U.S. Pat. No. 4,940,723, serine protease inhibition can be used for the treatment of clinical arthritis, synovitis and associated pathologies. By comparing the activity of the subject compositions with BABIM, the compound described in the '723 patent, one can employ relevant concentrations of the subject compositions. For example, the amount of BABIM employed with rats was 10 mg/kg of body weight and the concentration of the subject compounds would be adjusted in accordance with their relative activity in relation to BABIM. One can relate the Ki of the subject compound with the Ki of BABIM to determine an initial concentration for use, followed by optimization in accordance with known ways.

The subject compositions also permit investigation of the physiological processes associated with a wide variety of biological events involving serine proteases. The convenience of being able to inhibit serine proteases in the presence of zinc, while removing the inhibition in the absence of zinc, permits serine proteases to be turned on and off. Thus, one has the opportunity to investigate numerous physiological processes, in the presence and absence of active serine proteases. In addition, the subject compositions can be used in competition with other compounds, which may be antagonists, so as to be able to screen compounds having inhibitory activity.

For use in vivo, the subject compositions will be formulated as zinc complexes in appropriate physiological media, e.g., water, saline, phosphate buffered saline, vegetable oil, aqueous ethanol, or the like, except in those limiting cases in which the formulation components, buffers, excipients or solvent or solvent combination would cause precipitation of the zinc complex. Usually, however, solubility and complex formation are well maintained at or around physiological pH values. Various excipients may be included as is known in the art. The concentration of the particular compound will vary widely, depending upon the manner of administration, the indication for which it is being used, the frequency of administration, the activity of the compound being employed, and the like. Therefore, for each compound and each indication, the formulation will be optimized for the particular purpose. Generally, the inhibitor will be present in at least about 0.01 weight % and not more than about 50 weight %, usually not more than about 5 weight %.

The following examples are offered by way of illustration and not by way of limitation.

Experimental

The assay for the determination of Ki of trypsin was performed as follows:

Baseline Assay Format

Two 96-well microtiter plates are used for the enzyme assays. Enzyme and substrate are added to the assay plate and inhibitor concentration is varied in a dilution plate (a single dilution plate is used for 2 assay plates). The candidate compound (~1 mg) is dissoloved in DMSO (200 µl) or distilled water (1.0 ml) and the stock concentration is calculated. The stock solution is diluted 1:10 into the first well of a 96-well microtiter plate (Falcon, cat#3918) (20 µl) and 180 µl of buffer added (in the first dilution, with the candidate compound dissolved in DMSO, the buffer is 50 mM Tris, pH 8.2, 100 mM NaCl, 0.05% Tween-20, while when dissolved in water, the buffer includes 10% DMSO). Seven serial 3-fold dilutions down a column of the plate (60 µl of the sample and 120 µl of buffer with DMSO) are carried out and the pH is confirmed to 8.0. 50 µl of sample from each well of the dilution plate is transferred to a corresponding well on the assay plate, followed by the addition of 25 µl of enzyme solution (Stock solution is diluted 1:160 in buffer with DMSO to provide a final trypsin concentration of 3.4 nM).

The assay plate is then wrapped in plastic wrap and the inhibitor (20 mM pentamidine in DMSO or candidate compound) incubated at room temperature for 1 hr. At the end of the incubation, 25 µl of substrate (N-tosyl-gly-pro-lys-pNA; Sigma #T6140, 0.5 mM in water) is added to provide a total volume of 100 µl. The plate is then inserted into a plate reader and the change in absorbance at 405 nm measured for five minutes.

Assay Format With Zinc Removed

The assay protocol for determination of inhibition in the enforced absence of zinc is identical to the above Baseline assay format, with the exception that the buffer mixture listed above is substituted by phosphate buffered saline, 0.05% Tween 20, 10% DMSO and 1 mM EDTA, adjusted to pH 8.0.

Assay Format With Zinc Added

The assay protocol for determination of inhibition in the enforced presence of zinc is identical to the above Baseline assay format, with the exception that the buffer mixture listed above is substituted by phosphate buffered saline, 0.05% Tween 20, 10% DMSO adjusted to pH 8.0. To this mixture is added 150 µM zinc chloride in the form of a stock solution of 100 mM concentration in water.

The candidate inhibitors were prepared based on the use of amidine as the P1 binding moiety and various nitrogen based chelating agents as the inhibiting moiety. Using the assay described above, the Ki for a number of these compounds was determined for trypsin inhibition. The following table indicates the results.

TABLE 1

Serine Protease Inhibition Data

| | Trypsin inhibition, (Ki, µM) | | |
|---|---|---|---|
| Compound | Baseline | Zn removed | Zn added |
| BABIM | 0.096 | 88.2 | 0.35 |
| 5-5'-bis(amidinobenzimidazole)carbonyl | 50 | 35 | 0.47 |
| benzamidine | 325 | 266 | 273 |
| 2,2'-bis-imidazole | >1000 | >1000 | 474 |
| 2-(2'-(5'-amidino)benzimidazolyl)methylbenzimidazole | 0.019 | 182 | 0.023 |
| benzylamine | >1000 | 344 | 354 |
| 2-(2'-(5'-amidino)benzimidazolyl)methylimidazole | >1000 | >1000 | 32.8 |
| 2-(2'-(5'-aminomethyl)benzimidazolyl)methyl-5-methylbenzimidazole | 808 | >1000 | 1.47 |
| 2-(2'-(5'-aminomethyl)benzimidazolyl)methyl-5-carboxybenzimidazole | 1.26 | >1000 | 1.93 |
| 2-(2'-pyridyl)-benzimidazole | >1000 | >1000 | >1000 |
| 2-(2'-(5'-amidino)benzimidazolyl)pyridine | 748 | 101 | 20.9 |

X-Ray Crystallallography of an Inhibitor-Zinc Complex Bond To Trypsin

Crystals of benzamidine-trypsin were grown using $MgSO_4$ as the precipitant in 100 mM Tris, pH 8.2 by the batch method of M. Krieger, L. M. Kay and R. Stroud, J. Mol. Biol. 83:209–230 (1974). BABIM-trypsin could not be crystallized de novo, nor with seeding with benzamidine-trypsin crystals. Initial attempts to soak BABIM into these crystals at pH 8.2 were unsuccessful because of limited solubility and stability of BABIM at this pH in $MgSO_4$-containing synthetic mother liquor. Moreover, in Tris buffer alone at pH 8.2 BABIM turns yellow within an hour, and after many hours begins to precipitate. In MES buffer at pH 5.9 this transformation does not occur after several weeks. The solubility of BABIM freshly dissolved in synthetic mother liquor containing 415 mg/ml MgSO4, 100 mM Tris, pH 8.2 or 415 mg/ml $MgSO_4$, 100 mM MES, pH 5.9 was determined to be ~100 mM.

Crystals of BABIM-trypsin (pH 5.9) were first prepared successfully by soaking benzamidine-trypsin crystals in freshly dissolved BABIM in synthetic mother liquor at saturation at pH 5.9. The soaks were replaced with fresh ones 4 times, about once a day. Crystals of BABIM-trypsin (PH 8.2) were successfully prepared by soaking benzamidine-trypsin crystals in freshly dissolved BABIM in synthetic mother liquor at saturation at pH 8.2 containing 0.1 mM $ZnSO_4$. The soaks were replaced with fresh ones 5 times, about once a day. Significant amounts of yellow precipitate formed in the soaking solutions after a day.

Individual $I_{hkl}$ data were collected for benzamidine-trypsin (pH 8.2), BABIM-trypsin (pH 5.9) and $Zn+^2$-BABIM-trypsin (pH 8.2) on a Siemens Multiwire Area Detector or on an image plate detector (R-axis-II (Rigaku Corporation)). Data were extracted using the XDS programs of Kabsch, or the software provided by the Macromolecular Structure Corporation, (Houston Tex.), and an indexing program. Data collection and refinement statistics are listed in Table 2.

For the refinement of benzamidine-trypsin, the highly refined MIP-trypsin structure served as a template. Water molecules outside the active site region in the MIP X-ray and neutron structures were included in the initial phasing model. The structure was refined using alternating cycles of ($|Fo|-|Fc|$), $\alpha_c$, and ($2|Fo|-|Fc|$), $\alpha_c$ difference maps (J. L. Chambers & R. Stroud, Acta Cryst. B35: 1861–1875 (1979), and automated least squares refinement with XPLOR (Brunger). Difference Fourier maps were computed between benzamidine-trypsin (pH 8.2) and BABIM-trypsin (pH 5.9) or $Zn^{+2}$-BABIM-trypsin (pH 8.2) to yield initial structures which were then likewise refined.

The ($2|Fo|-|Fc|$), $\alpha_c$ difference map for BABIM-trypsin at pH 5.9 clearly shows one amidinobenzimidazole group of BABIM occupying the P1 pocket. The benzamidine portion of it closely overlays that for benzamidine in the benzamidine-trypsin structure. At pH 8.2, the ($|Fo|-|Fc|$), $\alpha_c$ and ($2|Fo|-|Fc|$), $\alpha_c$ maps for the $Zn^{+2}$-BABIM-trypsin complex clearly reveal the position and orientation of BABIM as well as a strong peak (13σ in the ($|Fo|-|Fc|$), $\alpha_c$ map) which corresponds to the position of the $Zn^{+2}$ ion coordinating two of the imidazole nitrogens of BABIM, the imidazole of His57 and the Oγ atom of Ser195. Thus the nanomolar binding constant of BABIM is achieved with the snyergy of $Zn^{+2}$ at concentrations of this metal at lower than 100 nM. Bond distances involving the $Zn^{+2}$ ion, are similar to those observed in other $Zn^{+2}$-containing proteins. The average of 5 ligand-$Zn^{+2}$-ligand angles is 114(11)°, but the $6^{th}$ angle, involving the BABIM ligand alone (N3-$Zn^{+2}$-N3') is only 81°. The BABIM molecule pivots to an altered position in the structure of trypsin-BABIM-$Zn^{+2}$ at pH 8.2, to allow the benzimidazoles of BABIM to form part of the $Zn^{+2}$ binding site. The pivoting causes an insignificant change in the position of the amidine group in the P1 pocket, but a large shift (~5 Å) in the position of the other amidine group. An NH group of one terminal amidine nitrogen interacts with main chain carbonyl 41 through bridging hydrogen bonds, while another NH group of the other terminal amidine nitrogen forms a direct hydrogen bond with the main chain carbonyl 244 of a symmetry related molecule.

TABLE 2

Crystallography of Trypsin-Benzamidine, Trypsin-BABIM-$SO_4^{-2}$, pH 5.9, and Trypsin-BABIM-$ZN^{+2}$, pH 8.2

| | Trypsin-Benzamidine | | Trypsin-Babim-$SO_4^{-2}$ | Trypsin-Babim-$Zn^{+2}$ |
|---|---|---|---|---|
| | (1 BNZ) | (2 BNZ) | | |
| Parameters[a] | | | | |
| # Atoms (including disorder) | 4114[a] | 4095[a] | 1926 | 1955 |
| # Waters (including disorder) | 225 | 229 | 211 | 214 |
| # discretely disordered groups[b] | 23 | 18 | 20 | 21 |
| # discretely disordered waters | 2 | 5 | 4 | 7 |
| # side chains with refined occs[c] | 12 | 13 | 16 | 13 |
| # waters with refined occs | 90 | 91 | 0 | 0 |
| Diffraction Statistics | | | | |
| Resolution[d] (Å) | 8.00–1.50 | 7.00–1.70 | 8.00–1.77 | 8.00–2.04 |
| # Observations | | 63142 | | |
| # Reflections[d] | 24173 | 17697 | 12081 | 8337 |
| F/σ cutoff | 2.4 | 0 | 0 | 0 |
| $R_{merge}^e$ (%) | 16.1 | 15.4 | 13.4 | 15.8 |
| $R_{cryst}^f$ (%) | | | | |
| Completeness[e] (%) | 69.2 | 69.4 | 55.9 | 55.6 |
| rms deviations[g] | | | | |
| Bond lengths (Å) | 0.016 | 0.016 | 0.014 | 0.017 |
| Bond angles (°) | 3.7 | 3.7 | 2.9 | 3.8 |
| Torsion angles (°) | 26.7 | 26.3 | 26.1 | 26.4 |

[a]Restrained, isotropic temperature factors were refined for all structures. Hydrogen atoms were included in the refinement of the trypsin-benzamidine structures.
[b]not including waters.
[c]Density for all side chain atoms or for terminal atoms in these groups was weak absent and temperature factors were high. Discretely disordered groups are not included in this category. Occupancies for poorly defined atoms were refined.
[d]refers to refinement limits.
[e]$R_{merge} = \Sigma_h\Sigma_i|I(h)_i - <I(h)>|/\Sigma_h\Sigma I(h)_i$, where $I(h)_i$ is the ith observation of the intensity of reflection h.
[f]$R_{cryst} = \Sigma(F_o-F_c)/\Sigma F_o$.
[g]Root mean square deviations from ideal bond lengths and bond angles.

It is evident from the above results, that by using metal ion complexes, particularly zinc, or metal ion complexes, particularly zinc, in combination with compounds comprising a P site binding moiety and a metal ion chelating moiety, which compounds can fit at the active site, extremely active serine protease inhibitors can be produced. By modifying the P site binding moiety, the chelating compounds can be directed to a variety of different serine proteases with high specificity. In this manner, one may inhibit serine protease activity in vitro and in vivo, in studying physiological processes, in preventing degradation of proteins which are specific substrates of serine proteases, in inhibiting bacteriological action, and in treating a variety of indications, where the pathology is associated with active serine proteases.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for inhibiting a catalytic activity of a serine protease with a serine protease inhibitor in a medium comprising the serine protease and the inhibitor, wherein the inhibitor comprises a compound of Formula (a):

$$\{(B_p)_r - (I)\}_n (Y)_q \quad (a)$$

in which:
- n is 1 or 2;
- r is 0 or 1, with the proviso that at least one $B_P$ is present;
- q is 0 when n is 1 and q is 1 when n is 2;
- Y is a bond or linking group of from 1 to 6 atoms;
- I is a moiety that when n is 1 comprises at least two heteroatoms that are within 2 to 4 atoms of each other and when n is 2 comprises at least one heteroatom which is within 1 to 3 atoms of Y; and
- $B_P$ is a binding moiety attached to the I moiety for binding to one or more P sites of the serine protease and is within 1 to 6 atoms from the zinc chelating heteroatom comprising the I moiety to which the $B_P$ binding moiety is attached; the improvement which comprises (i) having sufficient zinc in the medium, (ii) adding sufficient zinc to the medium or (iii) providing the inhibitor to the medium as a zinc complex, such that the inhibitor, the zinc and a catalytic site of the serine protease form a ternary complex whereby the catalytic activity of the serine protease is inhibited.

2. The method according to claim 1, wherein the inhibitor comprises a compound of Formula (a) wherein n is 2, at least one I moiety is a fused or non-fused, mono- or polycyclic moiety of 2 to 36 carbon atoms, wherein each individual ring comprising the cyclic moiety contains 4 to 7 annular members, and the zinc chelating heteroatoms are N, O or S and are each 1 to 3 atoms from Y and 1 to 6 atoms from any $B_P$ binding moiety attached to that I moiety to which each chelating heteroatom comprises.

* * * * *

UNITED STATES PATENT AND TRADEMARK OFFICE
CERTIFICATE OF CORRECTION

PATENT NO. : 5,900,371
DATED : May 4, 1999
INVENTOR(S) : James M. Clark, et. al.

It is certified that error appears in the above-identified patent and that said Letters Patent is hereby corrected as shown below:

Title page, item [73] Assignee: line 1, after "Inc.," insert --So.--.

Signed and Sealed this

Eighth Day of February, 2000

Attest:

Q. TODD DICKINSON

*Attesting Officer*  *Commissioner of Patents and Trademarks*